United States Patent
Liu et al.

(10) Patent No.: US 11,650,188 B2
(45) Date of Patent: May 16, 2023

(54) METHOD, APPARATUS, AND SYSTEM FOR RECOVERING A SENSOR FROM SILICONE POISONING

(71) Applicant: Rae Systems, Inc., Sunnyvale, CA (US)

(72) Inventors: Ling Liu, Charlotte, NC (US); Na Wei, Charlotte, NC (US); Fucheng Zhang, Charlotte, NC (US)

(73) Assignee: RAE SYSTEMS INC., Sunnyvale, CA (US)

( * ) Notice: Subject to any disclaimer, the term of this patent is extended or adjusted under 35 U.S.C. 154(b) by 153 days.

(21) Appl. No.: 17/303,424

(22) Filed: May 28, 2021

(65) Prior Publication Data
US 2021/0396727 A1 Dec. 23, 2021

(30) Foreign Application Priority Data
Jun. 19, 2020 (CN) .......................... 202010566723.3

(51) Int. Cl.
*G01N 33/00* (2006.01)
*G01N 27/16* (2006.01)

(52) U.S. Cl.
CPC ........... *G01N 33/005* (2013.01); *G01N 27/16* (2013.01)

(58) Field of Classification Search
CPC .............................. G01N 37/16; G01N 33/005
USPC ........................................................... 73/232
See application file for complete search history.

(56) References Cited

U.S. PATENT DOCUMENTS

| 5,858,306 A * | 1/1999 | Oh .......................... G01N 27/16 422/51 |
| 6,060,025 A | 5/2000 | Pasquariello |
| 2019/0025233 A1* | 1/2019 | Tanaka ................... G01N 25/30 |
| 2019/0025270 A1* | 1/2019 | Tanaka ................... B01J 20/103 |

FOREIGN PATENT DOCUMENTS

| CN | 101445251 A | 6/2009 |
| CN | 105606656 A | 5/2016 |
| CN | 108387625 A | 8/2018 |
| JP | 2012037413 A | * 2/2012 |

OTHER PUBLICATIONS

Translation of JP-2012037413-A (Year: 2012).*
Honeywell Rae Systems, Technical Note TN-206 09/18/VK, Extending Life of LEL Sensors in Field Conditions, 3 pgs.

* cited by examiner

*Primary Examiner* — Nathaniel T Woodward
(74) *Attorney, Agent, or Firm* — Alston & Bird LLP

(57) ABSTRACT

Various embodiments described herein relate to methods, apparatuses, and systems for recovering gas sensors from silicone poisoning. In an example embodiment, a method of recovering a gas sensing apparatus from silicone poisoning is provided. The method includes exposing the gas sensing apparatus to a predetermined hydrogen concentration for a period of hydrogen exposure time. The predetermined hydrogen concentration breaks down the silicon oxide bonds formed on a catalytic bead of the gas sensing apparatus. The method also includes providing a methane concentration to the gas sensing apparatus for a period of methane exposure time. The method further includes determining that the gas sensing apparatus satisfies a predetermined calibration sensitivity based on the reaction of the gas sensing apparatus to the methane concentration.

26 Claims, 6 Drawing Sheets

METHOD, APPARATUS, AND SYSTEM FOR RECOVERING A SENSOR FROM SILICONE POISONING

CROSS-REFERENCE TO RELATED APPLICATIONS

This application claims priority pursuant to 35 U.S.C. 119(a) of China Patent Application No. 202010566723.3, filed Jun. 19, 2020, which application is incorporated herein by reference in its entirety.

FIELD OF THE INVENTION

The present disclosure relates generally to methods, apparatuses, and systems for recovering a sensor from silicone poisoning and more particularly, to methods, apparatuses, and systems for using hydrogen to recover a sensor from silicone poisoning.

BACKGROUND

A gas sensor is a device that may detect the presence and/or concentration level of gaseous substance, including, for example, combustible gas, flammable gas, and/or toxic gas. For example, a low explosive limit (LEL) gas sensor may measure the concentration level of combustible and/or flammable gaseous substance (such as, for example, propane, and methane) up to one-hundred-percent (100%) of the low explosive limit of the gaseous substance. The term "lower explosive limit" refers to the minimum concentration level of gaseous substance in the air to support combustion when there is a source of ignition. Applicant has identified a number of deficiencies and problems associated with current LEL gas sensors. Through applied effort, ingenuity, and innovation, many of these identified problems have been solved by the methods and apparatus of the present disclosure.

BRIEF SUMMARY

Various embodiments described herein relate to methods, apparatuses, and systems for recovering gas sensors from silicone poisoning. In an example embodiment, a method of recovering a gas sensing apparatus from silicone poisoning is provided. The method includes exposing the gas sensing apparatus to a predetermined hydrogen concentration for a duration of hydrogen exposure time. The predetermined hydrogen concentration breaks down the silicon oxide bonds formed on a catalytic bead of the gas sensing apparatus. The method also includes providing a methane concentration to the gas sensing apparatus for a period of methane exposure time. The method further includes determining that the gas sensing apparatus satisfies a predetermined calibration sensitivity based on the reaction of the gas sensing apparatus to the methane concentration.

In some embodiments, exposing the gas sensing apparatus to a predetermined hydrogen concentration for a duration of hydrogen exposure time occurs in an instance in which there is silicone contamination resource. In some embodiments, the predetermined hydrogen concentration is from 1.8% to 4% Hydrogen dioxide by volume. In some embodiments, the period of hydrogen exposure time is from 10 seconds to 3 minutes. In some embodiments, the methane concentration is provided to the gas sensing apparatus after the gas sensing apparatus is exposed to the hydrogen concentration. In some embodiments, the methane concentration is greater than 2.5% volume of methane. In some embodiments, each step of claim 1 is repeated at a regular interval. In some embodiments, the regular interval is between 1 day and 1 month. In some embodiments, in an instance in which the gas sensing apparatus does not satisfy the predetermined calibration sensitivity, the method also includes repeating each step discussed above.

In some embodiments, the gas sensing apparatus is a low explosive level sensor. In some embodiments, the gas sensing apparatus has a voltage from 2 Volts to 5 Volts. In some embodiments, the gas sensing apparatus is a non-silicone based low explosive level sensor. In some embodiments, the gas sensing apparatus includes a carrier made at least partially out of aluminum.

In another example embodiment, a recovery apparatus configured to recover a gas sensing apparatus from silicone poisoning is provided. The recovery apparatus includes at least one processor configured to expose the gas sensing apparatus to a predetermined hydrogen concentration for a duration of hydrogen exposure time. The predetermined hydrogen concentration breaks down the silicon oxide bonds formed on a catalytic bead of the gas sensing apparatus. The recovery apparatus is also configured to provide a methane concentration to the gas sensing apparatus for a period of methane exposure time. The recovery apparatus is further configured to determine that the gas sensing apparatus satisfies a predetermined calibration sensitivity based on the reaction of the gas sensing apparatus to the methane concentration.

In some embodiments, exposing the gas sensing apparatus to a predetermined hydrogen concentration for a duration of hydrogen exposure time occurs in an instance in which there is silicone contamination resource. In some embodiments, the predetermined hydrogen concentration is from 1.8% to 4% Hydrogen dioxide by volume. In some embodiments, the period of hydrogen exposure time is from 10 seconds to 3 minutes. In some embodiments, the methane concentration is provided to the gas sensing apparatus after the gas sensing apparatus is exposed to the hydrogen concentration. In some embodiments, the methane concentration is greater than 2.5% volume of methane. In some embodiments, each step of claim 1 is repeated at a regular interval. In some embodiments, the regular interval is between 1 day and 1 month. In some embodiments, in an instance in which the gas sensing apparatus does not satisfy the predetermined calibration sensitivity, the recovery apparatus is further configured to repeat each step discussed above.

In some embodiments, the gas sensing apparatus is a low explosive level sensor. In some embodiments, the gas sensing apparatus has a voltage from 2 Volts to 5 Volts. In some embodiments, the gas sensing apparatus is a non-silicone based low explosive level sensor. In some embodiments, the gas sensing apparatus includes a carrier made at least partially out of aluminum.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which.

DETAILED DESCRIPTION OF THE INVENTION

Figure 1A:
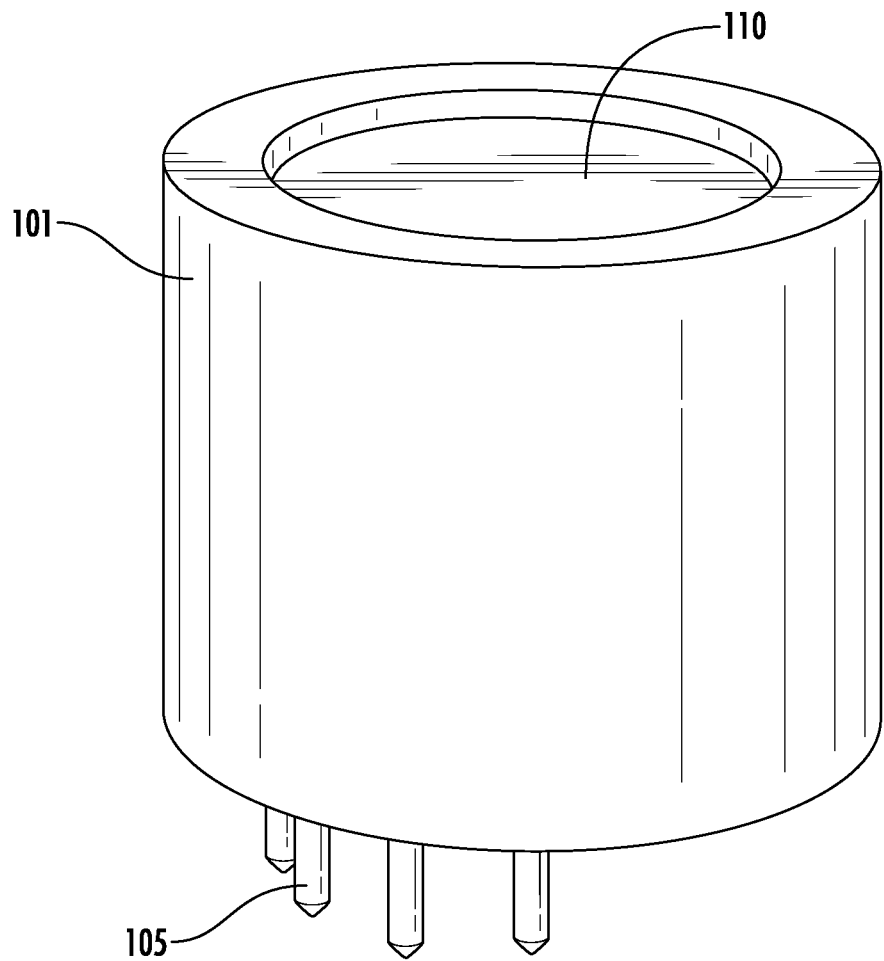
FIG. 1A illustrates an example exterior view of an example gas sensing apparatus in accordance with various embodiments of the present disclosure.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

The phrases "in one embodiment," "according to one embodiment," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such component or feature may be optionally included in some embodiments, or it may be excluded.

Many factors may affect the accuracies and life span of gas sensor readings. Gas sensors, and specifically LEL sensors rely on catalytic beads, that in operation, react with silicone that accumulates in the sensor over time (e.g., based on silicone in a gas mixture during detection, based on the environment, and/or during a storage period) to form silicone dioxide. As a result and in various example embodiments, bonds may be present in a catalytic bead that is part of silicone poisoned gas sensing apparatus 100. Such bonds may include, but are not limited to silicone dioxide, silicone-aluminum (Si—Al), and/or carbon-aluminum (C—Al). In some examples, the existence of silicone dioxide or other example bonds in the sensor cause the sensitivity of the sensor to be decreased (e.g., silicon poisoning). Additionally, the silicone poisoning may result in a gradual catalyst (e.g., aluminum) degradation or deactivation which may result in loss of sensitivity.

As is described herein, various example embodiments are designed to reverse or otherwise overcome silicone poisoning. For example, example methods described herein may provide a hydrogen concentration as part of a bump test to break down the silicon dioxide bonds and, in some examples, recover the sensor from silicone poisoning. Further, a methane concentration may be applied to monitor the gas concentration thereafter. Advantageously, and in some examples, the example methods may be repeated over the life of the sensor, increasing the lifespan of the sensor and allowing for silicone poisoning recovery and, in some examples an increase in sensitivity of the sensor.

Referring now to FIG. 1, an example gas sensing apparatus 100 in accordance with various embodiments of the present disclosure is shown. In particular, the example gas sensing apparatus 100 may be a low explosive limit (LEL) sensor that is configured to detect and measure the concentration level of one or more combustible gaseous substances (e.g., methane, propane, n-butane, n-pentane, n-hexane, n-octane, gasoline, hydrogen, acetone, ethanol, m-xylene, toluene, benzene, styrene, and/or the like).

The example gas sensing apparatus 100 as shown in FIG. 1A may comprise a sensor housing 101, a cover member 110, and connection pin(s) 105. The cover member 110 may be made of a material that has flame-proof properties and comprise porous structures, such as, for example, sintered stainless steel or sintered metallic fibers. The cover member 110 may be in contact with the gaseous substance that the example gas sensing apparatus 100 is configured to detect and/or measure. The porous structures of the cover member 110 may allow the gaseous substance to pass through the cover member 110 and enter into the example gas sensing apparatus 100. The flame-proof properties of the cover member 110 may prevent any combustion and/or flame that occurred within the example gas sensing apparatus 100 from spreading outside the gas sensing apparatus 100.

The sensor housing 101 of the example gas sensing apparatus 100 may be made of a metal alloy, such as stainless steel or carbon steel. In some examples, the sensor housing 101 may be in a shape similar to a hollow cylinder shape. In some examples, the sensor housing 101 may be in other shapes, such as but not limited to a hollow hexagonal prism shape, a hollow cube shape, without deviating from the scope of the present disclosure. The sensor housing 101, together with the cover member 110, may form an enclosure that houses various components of the example gas sensing apparatus 100, such as those discussed in reference to FIG. 1B.

In various embodiments, the example gas sensing apparatus 100 may comprise one or more metal connection pins 105 that are connected to electronic element(s) within the example gas sensing apparatus 100 (such as, for example, metal wire coils of the bead members disposed on the header plate), and may transmit electronic signals associated with these electronic element(s) to one or more other circuitries. As discussed in reference to FIG. 1B, the connection pin(s) 105 may be connected to a printed circuit board (PCB) 104 within the sensor 100. While FIG. 1 illustrates the example gas sensing apparatus 100 as having at least four connection pins 105 and FIG. 1B illustrates the example gas sensing apparatus 100 as having three connection pins 105, various embodiments may have a different number of connection pins without deviating from the scope of the present disclosure.

Additionally or alternatively, the example gas sensing apparatus 100 may comprise one or more connection wires. The connection wires may be connected to electronic element(s) within the example gas sensing apparatus 100 (such as, for example, metal wire coils of the bead members disposed on header plate), and may transmit electronic signals associated with these electronic element(s) to one or more other circuitries.

In various embodiments, the gas sensing apparatus may be configured to perform the steps discussed herein. In various embodiments, the LEL gas sensing apparatus 100 may have a voltage from 2 Volts to 5 Volts. In various embodiments, the LEL gas sensing apparatus 100 may have a voltage from 2 Volts to 3 Volts. In various embodiments, the LEL gas sensing apparatus 100 may have a voltage from 3 Volts to 4 Volts. In various embodiments, the LEL gas sensing apparatus 100 may have a voltage from 4 Volts to 5 Volts. In various embodiments, the gas sensing apparatus 100 may be a 2.3 Volt LEL gas sensing apparatus. In various embodiments, the gas sensing apparatus 100 may be a 4.25 Volt LEL gas sensing apparatus.

Figure 1B:
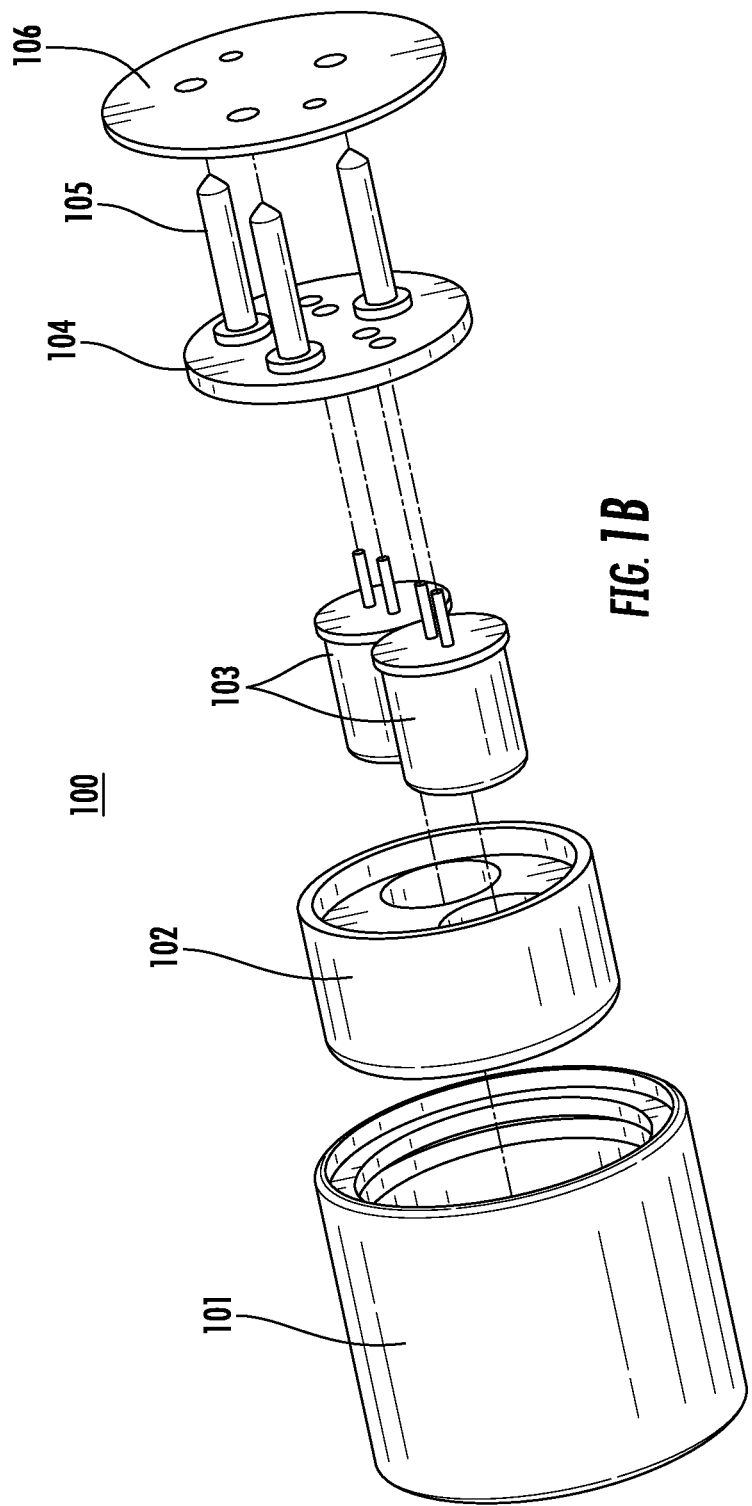
FIG. 1B illustrates an example exploded view of an example gas sensing apparatus in accordance with various embodiments of the present disclosure

Referring now to FIG. 1B, an exploded view of an example gas sensing apparatus 100 is shown. As shown, the gas sensing apparatus 100 may include a sensor housing 101, a LEL element housing 102, one or more LEL elements 103, a printed circuit board (PCB) 104, one or more connection pins 105, and a sensor cover 106.

In various embodiments, the sensor housing 101 is configured to receive the LEL element housing 102, the one or more LEL elements 103, and the PCB 104. In various embodiments, the sensor cover 106 may be configured to be operably coupled to the sensor housing 101, such that the LEL element housing 102, the one or more LEL elements 103, and the PCB 104 are disposed within the sensor 100. In various embodiments, the sensor cover 106 may have one or more connection pin receiving apertures configured to receive the connection pin(s) 105, such that the connection pins 105 may be attached to the PCB 104 at a first end of the pin, while the opposite end of the pin may extend out of the sensor housing 101, as shown in FIG. 1A.

Figure 3:
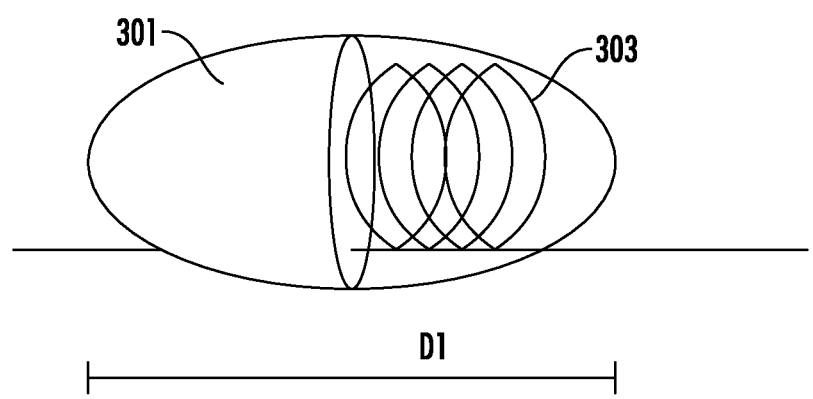
FIG. 3 illustrates an example diagram of various components of an example gas sensing apparatus in accordance with various embodiments of the present disclosure.

As discussed in more detail in reference to FIG. 3, the LEL element(s) 103 may be disposed within the LEL element housing 102. In various embodiments, the LEL element(s) 103 may be operably coupled to the PCB 104, such that the LEL element(s) 103 are in communication with the PCB 104. In various embodiments, the LEL element housing 102 may be configured to house a plurality of LEL elements 103, such as the two LEL elements 103 shown in FIG. 1B.

The printed circuit board 104 may be disposed beneath the sensor cover 106. The printed circuit board 104 may mechanically support and electrically connect various electronic components (such as, for example, various electronic components for a sensing circuitry). Further, the LEL element 103 may be connected to various electronic components on the printed circuit board 307 (such as the sensing circuitry) through, for example, metal leads. Example metal leads are illustrated and described below in connection with FIG. 2. In various embodiments, the gas may access the LEL element 103 by passing through the cover member 110 of the gas sensing apparatus 100.

Figure 2:
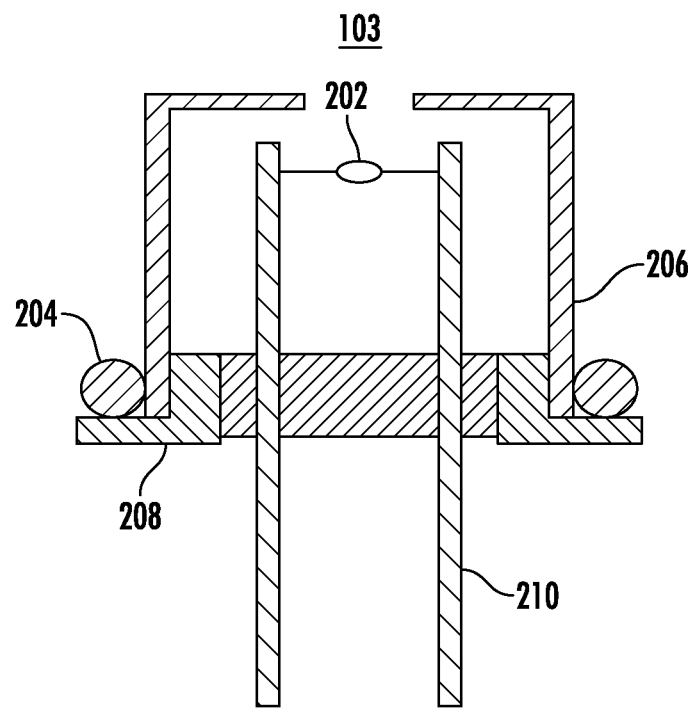
FIG. 2 illustrates an example diagram of various components of an example gas sensing apparatus in accordance with various embodiments of the present disclosure.

Referring now to FIG. 2 and FIG. 3, example diagrams illustrating various example LEL elements 103 used in an example gas sensing apparatus 100 are provided.

In the embodiment as shown in FIG. 2, the bead member 202 may be connected to a pair of metal leads 210. In particular, the metal leads 210 may be connected to the metal wire coil within the bead member 202, and the metal leads 210 may comprise material, such as platinum or palladium. In various embodiments, the bead member 202 may have a non-silicone carrier (e.g., the bead 301), such as aluminum ($Al_2O_3$), for the catalyst to be coated thereon. In various embodiments, additional additives may be present in the bead member 202 (e.g., $ZrO_2$, $CeO_2$, and/or the like).

In some examples, the ends of the metal leads 210 may be connected to various electronic components, such as, for example, the PCB 104 shown in FIG. 1B. Further, the bead member 202 may be housed within a container member 206. The container member 206 may be made of metal, and may further comprise an aperture that allows the bead member 202 to be in contact with the to-be-detected gaseous substance. In some examples, the container member 206 may be secured to a header plate 208 through a sealing ring 204. The sealing ring 204 may comprise elastic material, such as, for example, rubber and/or silicon.

Referring now to FIG. 3, an example internal structure of an example bead member 202 is shown. In particular, FIG. 3 provides a half cross-sectional view that illustrates a metal wire coil 303 disposed within a bead 301.

As described above, an example gas sensing apparatus may comprise two bead members. One of the bead members (the "detector element") may have a bead 301 that comprises catalytic material. The catalytic material may allow catalytic combustion or oxidation to occur. In various embodiments, the catalytic material may be a compound comprising palladium, platinum, and/or the like. In various embodiments, the catalytic material may be coated onto a carrier material, such as aluminum ($Al_2O_3$). In this regard, when a voltage is supplied to the metal wire coil 303, the metal wire coil 303 may heat the bead member. When the voltage is high enough, the high temperature of the bead member may cause the combustible gaseous substance to react on the detector element (such as catalytic oxidation). In various embodiments, the detector element may experience silicone poisoning in an instance silicone is present in the environment.

The other bead member (the "compensator element") may have a bead 301 that comprises non-catalytic material, but may otherwise resemble the detector element in other respects. In other words, the compensator element does not trigger catalytic combustion or oxidation, and the combustible gaseous substance may remain inert on the compensator element. In various embodiments, the compensator element may be configured to have no response to combustible gas, such that little to no silicone poisoning occurs on the compensator element.

In some examples, the length D1 of the bead member may be approximately one millimeter (1 mm). In some examples, the length D1 may be of other suitable value, without deviating from the scope of the present disclosure.

Figure 4A:
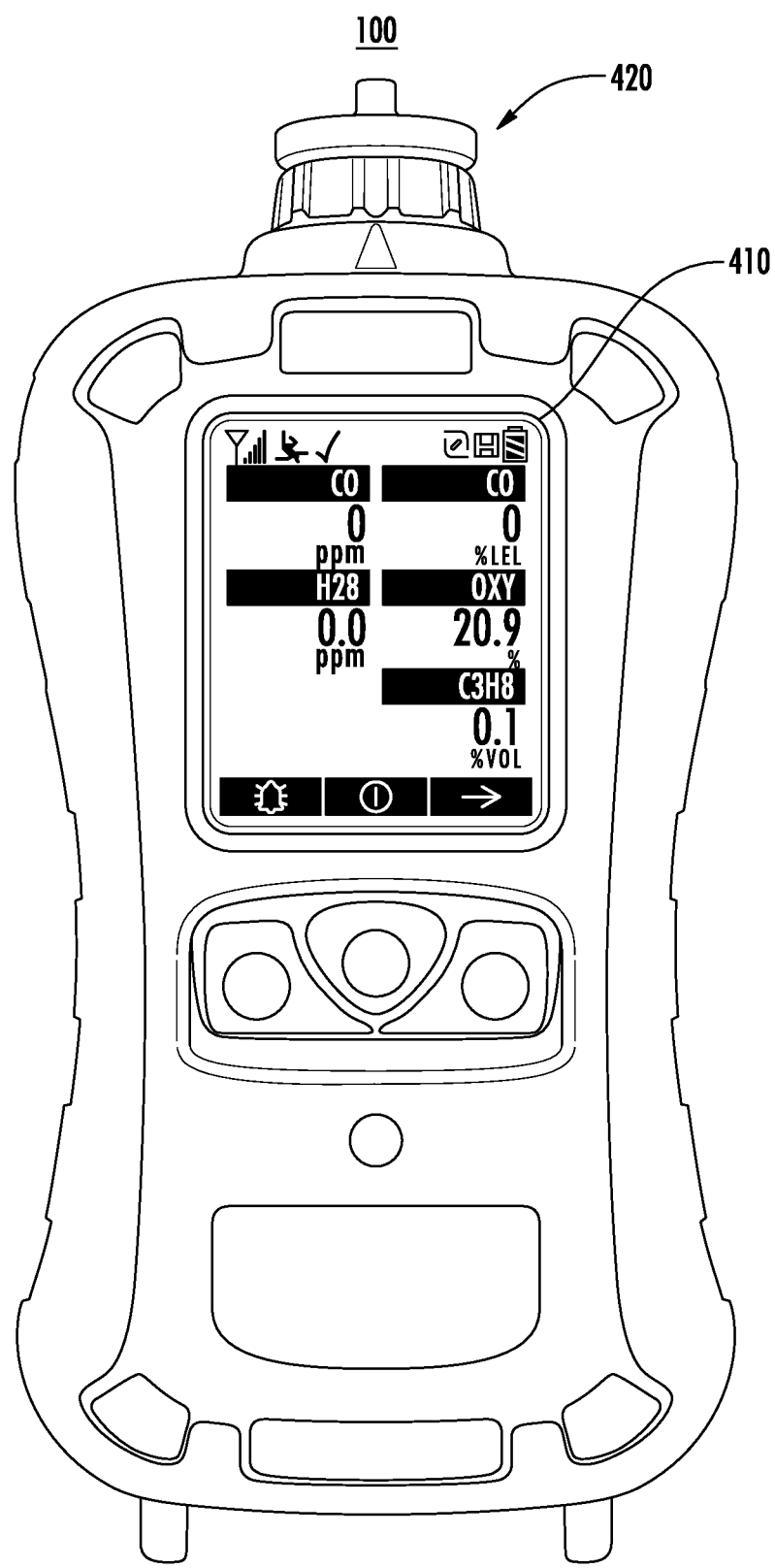
FIG. 4A illustrates an example recovery apparatus of various embodiments configured to carry out the operations of FIG. 5.

Referring now to FIG. 4A, an example recovery apparatus 400 is provided for use in communication with the gas sensing apparatus 100 discussed above. In various embodiments, the recovery apparatus 400 may be configured to provide a hydrogen concentration and/or a methane concentration to the gas sensing apparatus 100 as a part of a bump test or a calibration test, such that any silicon dioxide may decompose, such that the gas sensing apparatus 100 may operate effectively without silicone poisoning. In some examples, the bump test may be activated as often as desired, with the only limitation being the amount of gas releasing material available or any electrical or battery power limitations. The bump test may be performed every few minutes, hourly, daily, weekly, etc.

Figure 4B:
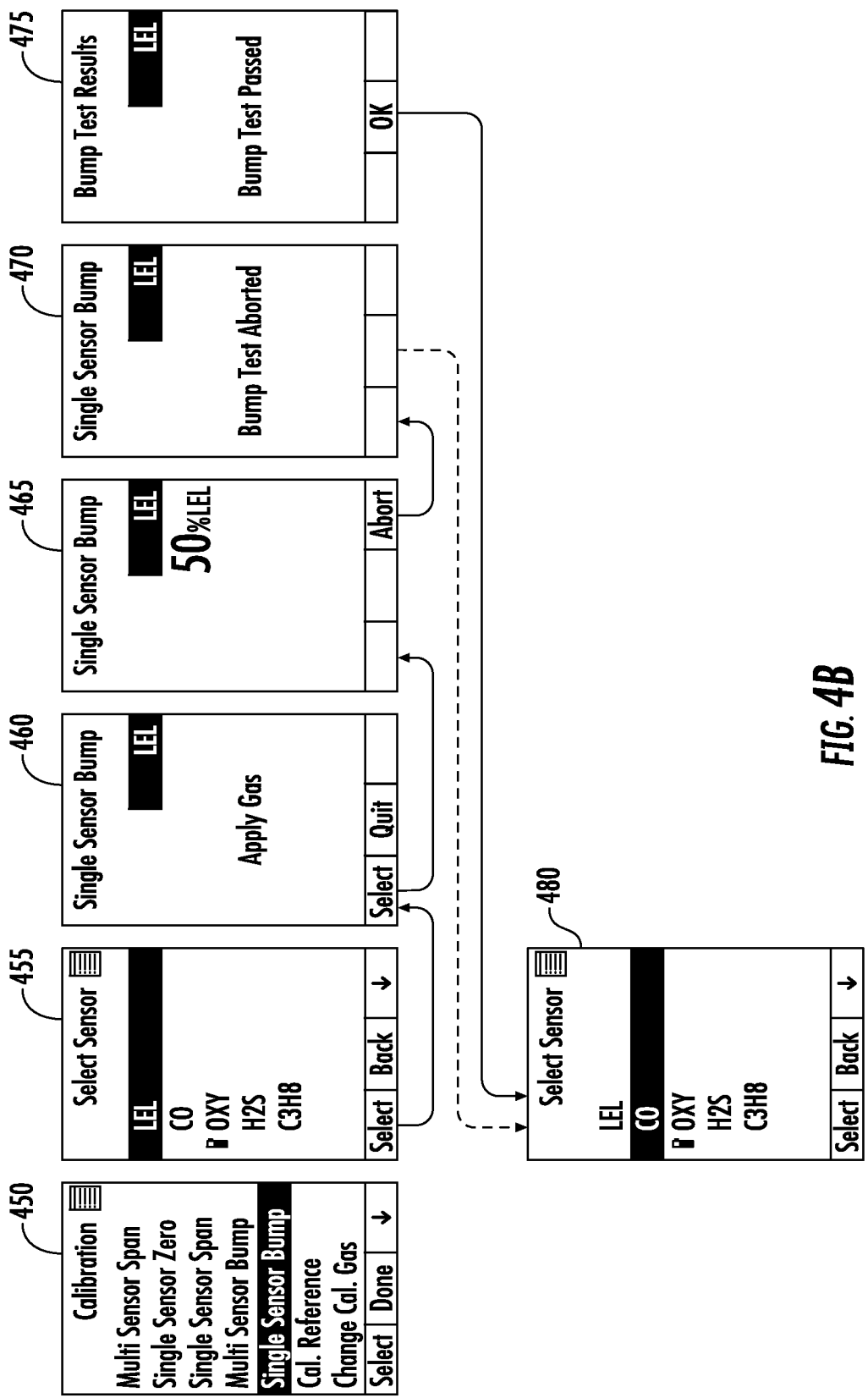
FIG. 4B illustrates an example screen in an instance in which the recovery method discussed in FIG. 5 is being carried out on a recovery apparatus.

In various embodiments, the components of the recovery apparatus 400 and the gas sensing apparatus 100 may be disposed in the same housing (e.g., the components of the gas sensing apparatus 100 discussed above may be disposed within the recovery apparatus 400). For example, as shown, the recovery apparatus 400 may include a gas inlet 420 configured to allow gas to enter the recovery apparatus 400 and be provided to one or more gas sensing apparatuses 100 within the recovery apparatus. In various embodiments, the recovery apparatus 400 may comprise various gas chambers configured to house one or more gas concentrations (e.g., hydrogen concentration and/or methane concentration discussed below). For example, the recovery apparatus 400 may have a four gas bottle, containing CO, $H_2S$, $O_2$, and methane, and an $H_2$ gas bottle used for the operations discussed herein. In various embodiments, the recovery apparatus 400 may comprise an activation mechanism 405 (e.g., a screen as shown in FIGS. 4A and 4B) configured to activate and/or view the results of the method discussed in FIG. 5.

In various embodiments, the recovery apparatus 400 may be configured with various means such as hardware, firmware, circuitry and/or other devices associated with execution of software including one or more computer program instructions. In some examples, the hardware, firmware, circuitry and/or other devices may be configured to operate a bump test or calibration test in accordance with the systems and methods described herein. In some examples, the systems and methods described herein may further be configured to recover the sensor, such as is described with respect to FIG. 5.

In some examples, the recovery apparatus 400 may include one or more processors (not shown) configured to carried out computer program instructions, which may be stored by a memory circuitry (such as a non-transitory memory) of the recovery apparatus 400 employing an embodiment of the present disclosure and executed by a processing circuitry (such as a processor) of the system. These computer program instructions may direct the system to function in a particular manner, such that the instructions stored in the memory circuitry produce an article of manufacture, the execution of which implements the function specified in the flowchart block(s). Further, the recovery apparatus 400 may comprise one or more other circuitries. Various circuitries of the recovery apparatus 400 (such as the sensing circuitry, the processing circuitry, and the memory circuitry) may be in electronic communication between and/or among each other to transmit data to and/or receive data from each other.

In some examples, embodiments of the recovery apparatus 400 may comprise a computer program product on a non-transitory computer-readable storage medium storing computer-readable program instructions (e.g. computer software). Any suitable computer-readable storage medium may be utilized including non-transitory hard disks, CD-ROMs, flash memory, optical storage devices, or magnetic storage devices.

Referring now to FIG. 4B, an activation mechanism (e.g., screen 410) sequence is shown in accordance with an example embodiment. As shown, the user may be able to select the bump test (e.g., recovery method of FIG. 5) as shown on screen 450. In various embodiments, the user may be able to select one or more sensors to perform the method as shown on screen 455. In various embodiments, the recovery apparatus 400 may be configured to select begin the recovery method as shown in screen 460 and monitor the sensitivity during testing in screen 465. In various embodiments, the recovery apparatus 400 may be configured to abort the recovery method during operation (e.g., as shown on screen 470). In various embodiments, the recovery apparatus 400 may be configured to notify the user that the results of the bump test (e.g., screen 475 displaying "Bump Test Passed"). In various embodiments, the recovery apparatus 400 may allow the user to select from additional sensors to perform the operations once the recovery method is complete on a given gas sensing apparatus (e.g., as shown on screen 480).

Figure 5:
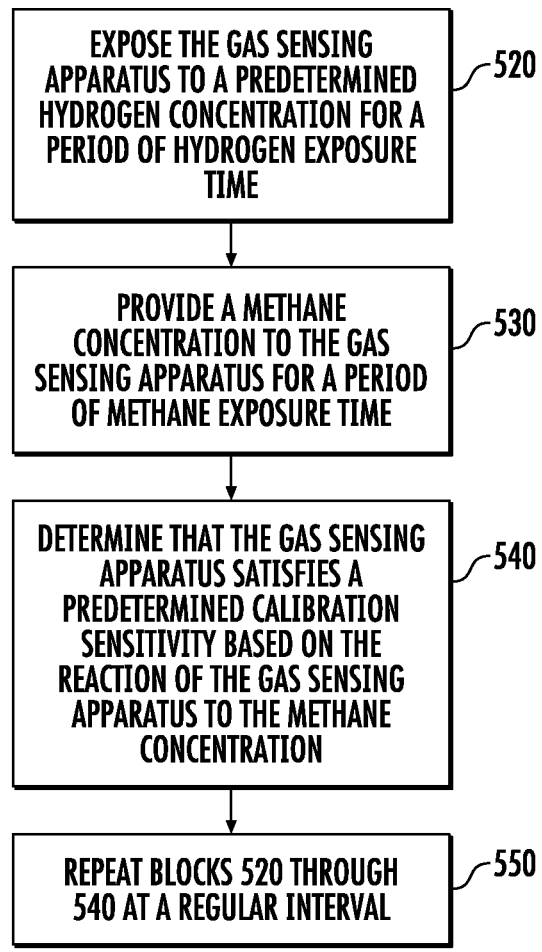
FIG. 5 illustrates an example flow chart in accordance with various embodiments of the present disclosure.

Referring now to FIG. 5, an example method associated with recovering a gas sensing apparatus from silicone poisoning. In various embodiments, the steps discussed herein in reference to FIG. 5 may be carried out at least partially by a recovery apparatus 400 discussed in reference to FIG. 4A. In various embodiments, the recovery apparatus 400 may be configured to operate in communication with the gas sensing apparatus 100. In various embodiments, the methods discussed herein may be performed on a non-silicone based gas sensing apparatus. In various embodiments, the methods discussed herein may be performed on a LEL gas sensing apparatus, such as the LEL gas sensing apparatus described with respect to FIGS. 1-3.

In various embodiments, the gas sensing apparatus may be configured to perform the steps discussed herein. In various embodiments, the LEL gas sensing apparatus 100 may have a voltage from 2 Volts to 5 Volts. In various embodiments, the LEL gas sensing apparatus 100 may have a voltage from 2 Volts to 3 Volts. In various embodiments, the LEL gas sensing apparatus 100 may have a voltage from 3 Volts to 4 Volts. In various embodiments, the LEL gas sensing apparatus 100 may have a voltage from 4 Volts to 5 Volts. In various embodiments, the gas sensing apparatus 100 may be a 2.3 Volt LEL gas sensing apparatus. In various embodiments, the gas sensing apparatus 100 may be a 4.25 Volt LEL gas sensing apparatus.

In some examples, each block of the flowchart, and combinations of blocks in the flowchart, may be implemented by various means such as hardware, firmware, circuitry and/or other devices associated with execution of software including one or more computer program instructions. In some examples, each block of the flowchart, and combinations of blocks in the flowchart, may be performed manually.

As is described herein, gas sensors are susceptible to accumulating a silicone compound present in an operating environment. In various embodiments, the accumulated silicone compound may bond with materials in the gas sensing apparatus 100 (e.g., the aluminum bead 301), such that silicon oxide (e.g., silicon dioxide) may be produced. For example, in an instance in which the gas sensing apparatus 100 accumulates a sufficient amount of silicone, the silicone compound may react with the oxide surface of the beads 301 (e.g., aluminum oxide ($Al_2O_3$)) to form ammonia. In various embodiments, a series of oxygen atoms bonded with trimethylsilyl (($CH_3)_3Si^-$) groups.

In various embodiments, bonds may be present in a silicone poisoned gas sensing apparatus 100 that may include silicone-aluminum (Si—Al) and/or carbon-aluminum (C—Al). In various embodiments, the silicone compound may be a Bis(trimethylsilyl)amine (e.g., HMDS) compound. For example, the silicone compound may be a HMDS vapor. In various embodiments, the presence of the Si—Al and C—Al may cause the gas sensing apparatus 100 to be inaccurate due to a reduction in sensitivity of the gas sensing apparatus. As such, the steps of FIG. 5 may be applied, in some examples, to recover a gas sensing apparatus from silicone poisoning.

Referring now to Block 520 of FIG. 5, the method may include exposing a sensor to a predetermined hydrogen concentration for a period of hydrogen exposure time. In various embodiments, the predetermined hydrogen concentration (e.g., $H_2$) may break down the silicon dioxide bonds present in the gas sensing apparatus 100 during exposure. In various embodiments, the predetermined hydrogen concentration may breaks down the C—Al bonds present in the gas sensing apparatus 100. In various embodiments, the predetermined hydrogen concentration may be at least 1.8% Hydrogen dioxide ($H_2$) by volume. In various embodiments, the predetermined hydrogen concentration may be from 1.8% to 4% $H_2$ by volume. In various embodiments, the predetermined hydrogen concentration may be from 1.8% to 3% $H_2$ by volume. In various embodiments, the hydrogen concentration may be exposed to the gas sensing apparatus 100 for a period of hydrogen exposure time. In various embodiments, the period of hydrogen exposure time may be a sufficient amount of time to restore the sensitivity of the gas sensing apparatus 100 to at least 50%. In various embodiments, the period of hydrogen exposure time may be sufficient for the H2 to break down the Silicon oxide bonds, such that the gas sensing apparatus 100 may recover. In various embodiments, the period of hydrogen exposure time may be at least 10 seconds. In various embodiments, the period of hydrogen exposure time may be at least 30 seconds. In various embodiments, the period of hydrogen exposure time may be at least 60 seconds. In various embodiments, the period of hydrogen exposure time may be at least 90 seconds. In various embodiments, the period of hydrogen exposure time may be at least 120 seconds. In various embodiments, the period of hydrogen exposure time may be at least 150 seconds. In various embodiments, the period of hydrogen exposure time may be at least 180 seconds. In various embodiments, the period of hydrogen exposure time may be greater than 180 seconds.

Referring now to Block 530 of FIG. 5, the method may include providing a methane concentration to the sensor for a period of methane exposure time. In various embodiments, the methane concentration may identify the gas sensing apparatus status (e.g., the operations of Block 530 may allow the gas sensor apparatus to determine the sensitivity and compare with sensor calibration sensitivity to determine whether the sensor sensitivity has been reduced and/or lost). In various embodiments, the methane concentration may be provided to the gas sensing apparatus after the gas sensing apparatus is exposed to the hydrogen concentration. In various embodiments, the methane concentration may be greater than 2.5% volume of methane. In various embodiments, the period of methane exposure time may be at least 10 seconds. In various embodiments, the period of methane exposure time may be at least 30 seconds. In various embodiments, the period of methane exposure time may be at least 60 seconds. In various embodiments, the period of methane exposure time may be at least 90 seconds. In various embodiments, the period of methane exposure time may be at least 120 seconds. In various embodiments, the period of methane exposure time may be at least 150 seconds. In various embodiments, the period of methane exposure time may be at least 180 seconds. In various embodiments, the period of methane exposure time may be greater than 180 seconds.

Referring now to Block 540 of FIG. 5, the method may include determining that the gas sensing apparatus satisfies a predetermined calibration sensitivity based on the reaction of the gas sensing apparatus to the methane concentration. As discussed herein, in various embodiments, the recovery apparatus 400 may be configured to monitor the sensitivity of the gas sensing apparatus 100. In various embodiments, the recovery apparatus 400 may determine whether the silicone poisoning has been reduced and/or eliminated based on the sensitivity reading. In various embodiments, the determination that the gas sensing apparatus satisfies the predetermined calibration sensitivity may be in conjunction with the operations of Block 530 (e.g., the methane concentration may be used to determine the sensitivity of the gas sensing apparatus). In various embodiments, the predetermined calibration sensitivity may be a recovery of at least 50% of the original sensitivity. In various embodiments, the predetermined calibration sensitivity may be a recovery of at least 65% of the original sensitivity. In various embodiments, the predetermined calibration sensitivity may be a recovery of at least 80% of the original sensitivity.

Referring now to Block 550 of FIG. 5, the method may include repeating Block 520 through Block 540 at a regular interval. In various embodiments, the operations may be periodically performed to recover the gas sensing apparatus from silicone poisoning. In various embodiments, the frequency of the operations being performed may be based on the amount of silicone in the gas sensing apparatus environment. In various embodiments, the operations may be repeated more frequently in high silicone environments. In various embodiments, the operations may be repeated automatically (e.g., the controller may be programmed to perform the operations at a regular interval). Additionally or alternatively, the operations may be manually repeated (e.g., a user may manually activate the operations). In various embodiments, the regular interval of bump testing may be from 1 day to 1 month. In various embodiments, the operations of Block 520 through Block 540 may be repeated at regular intervals for the life span of the gas sensing apparatus 100. In various embodiments, the more frequent the regular interval, in some examples, the longer lifespan for a given gas sensing apparatus 100.

In various embodiments, the silicone compound may be accumulate in the gas sensing apparatus 100 and the silicone compound may decompose with the gas sensing apparatus 100 to result in silicone dioxide (e.g., the silicone decomposing with the carrier may cause inaccurate readings due to a reduction in sensor sensitivity). In some embodiments, the operations of Blocks 520 through Block 540 may be carried out at an instance in which a command is received from a user. In some embodiments, the silicone compound in the gas sensing apparatus 100 may accumulate to at least 10 ppm silicone compound (e.g., HMDS vapor) before the operations of Block 520 through Block 540 are carried out. In some embodiments, the silicone compound in the gas sensing apparatus 100 may accumulate to at least 20 ppm silicone compound (e.g., HMDS vapor) before the operations of Block 520 through Block 540 are carried out. In some embodiments, the silicone compound in the gas sensing apparatus 100 may accumulate to at least 100 ppm silicone compound (e.g., HMDS vapor) before the operations of Block 520 through Block 540 are carried out. In various embodiments, the sensitivity of the gas sensing apparatus 100 may be reduced to at least 50% based on the accumulation of silicone oxide before the bump test begins (e.g., the operations of Blocks 520-540 may be carried out in an instance in which the sensitivity has been reduced to at least 50%). In various embodiments, the silicone compound may accumulate in the gas sensing apparatus 100 until the gas sensing apparatus (e.g., the LEL elements 103) are effectively silicone poisoned.

It is to be understood that the disclosure is not to be limited to the specific embodiments disclosed, and that modifications and other embodiments are intended to be included within the scope of the appended claims. Although specific terms are employed herein, they are used in a generic and descriptive sense only and not for purposes of limitation, unless described otherwise.

The invention claimed is:

1. A method of recovering a gas sensing apparatus from silicone poisoning, the method comprising:
   exposing the gas sensing apparatus to a predetermined hydrogen concentration for a period of hydrogen exposure time, wherein the predetermined hydrogen concentration breaks down the silicon oxide bonds formed on a catalytic bead of the gas sensing apparatus;
   providing a methane concentration to the gas sensing apparatus for a period of methane exposure time; and
   based on the reaction of the gas sensing apparatus to the methane concentration, determining that the gas sensing apparatus satisfies a predetermined calibration sensitivity.

2. The method of claim 1, wherein exposing the gas sensing apparatus to a predetermined hydrogen concentration for a duration of hydrogen exposure time occurs in an instance in which there is silicone contamination resource.

3. The method of claim 1, wherein the predetermined hydrogen concentration is from 1.8% to 4% Hydrogen dioxide by volume.

4. The method of claim 1, wherein the period of hydrogen exposure time is from 10 seconds to 3 minutes.

5. The method of claim 1, wherein the methane concentration is provided to the gas sensing apparatus after the gas sensing apparatus is exposed to the hydrogen concentration.

6. The method of claim 1, wherein the methane concentration is greater than 2.5% volume of methane.

7. The method of claim 1, wherein each step of claim 1 is repeated at a regular interval.

8. The method of claim 7, wherein the regular interval is between 1 day and 1 month.

9. The method of claim 1, wherein in an instance in which the gas sensing apparatus does not satisfy the predetermined calibration sensitivity, the method further comprises repeating each step of claim 1.

10. The method of claim 1, wherein the gas sensing apparatus is a low explosive level sensor.

11. The method of claim 10, wherein the gas sensing apparatus has a voltage from 2 Volts to 5 Volts.

12. The method of claim 10, wherein the gas sensing apparatus is a non-silicone based low explosive level sensor.

13. The method of claim 1, wherein the gas sensing apparatus comprises a carrier made at least partially out of aluminum.

14. A recovery apparatus configured to recover a gas sensing apparatus from silicone poisoning, the recovery apparatus comprising one or more gas chambers and at least one processor configured to:
   expose the gas sensing apparatus to a predetermined hydrogen concentration for a period of hydrogen exposure time, wherein the predetermined hydrogen concentration breaks down the silicon oxide bonds formed on a catalytic bead of the gas sensing apparatus;
   provide a methane concentration to the gas sensing apparatus for a period of methane exposure time; and
   based on the reaction of the gas sensing apparatus to the methane concentration, determine that the gas sensing apparatus satisfies a predetermined calibration sensitivity.

15. The recovery apparatus of claim 14, wherein exposing the gas sensing apparatus to a predetermined hydrogen concentration for a duration of hydrogen exposure time occurs in an instance in which there is silicone contamination resource.

16. The recovery apparatus of claim 14, wherein the predetermined hydrogen concentration is from 1.8% to 4% Hydrogen dioxide by volume.

17. The recovery apparatus of claim 14, wherein the period of hydrogen exposure time is from 10 seconds to 3 minutes.

18. The recovery apparatus of claim 14, wherein the methane concentration is provided to the gas sensing apparatus after the gas sensing apparatus is exposed to the hydrogen concentration.

19. The recovery apparatus of claim 14, wherein the methane concentration is greater than 2.5% volume of methane.

20. The recovery apparatus of claim 14, wherein each step of claim 1 is repeated at a regular interval.

21. The recovery apparatus of claim 20, wherein the regular interval is between 1 day and 1 month.

22. The recovery apparatus of claim 14, wherein in an instance in which the gas sensing apparatus does not satisfy the predetermined calibration sensitivity, the recovery apparatus is further configured to repeat each step of claim 14.

23. The recovery apparatus of claim 14, wherein the gas sensing apparatus is a low explosive level sensor.

24. The recovery apparatus of claim 23, wherein the gas sensing apparatus has a voltage from 2 Volts to 5 Volts.

25. The recovery apparatus of claim 23, wherein the gas sensing apparatus is a non-silicone based low explosive level sensor.

26. The recovery apparatus of claim 14, wherein the gas sensing apparatus comprises a carrier made at least partially out of aluminum.

* * * * *